United States Patent [19]
Shook et al.

[11] Patent Number: 5,823,195
[45] Date of Patent: Oct. 20, 1998

[54] ANKLE PAD

[76] Inventors: C. David Shook, 718 Glendale Blvd., Mansfield, Ohio 44907; David J. Hoy, 1270 Rosedale Dr., Mansfield, Ohio 44906

[21] Appl. No.: 437,940

[22] Filed: May 9, 1995

[51] Int. Cl.[6] ................................................ A61F 13/06
[52] U.S. Cl. ........................................ 128/893; 128/894
[58] Field of Search ................................. 128/845, 846, 128/888, 892, 893; 602/5, 23, 27, 60, 61, 62, 63, 65, 66

[56] References Cited

U.S. PATENT DOCUMENTS

| | | |
|---|---|---|
| 398,892 | 3/1889 | Golden ............................ 602/65 |
| 4,590,932 | 5/1986 | Wilkerson ........................ 602/65 |
| 4,705,025 | 11/1987 | Dedo ............................... 128/882 |
| 5,092,347 | 3/1992 | Shaffer ............................ 128/893 |

*Primary Examiner*—Michael A. Brown
*Attorney, Agent, or Firm*—Woodling, Krost & Rust

[57] ABSTRACT

A medial ankle pad is provided for the medial side of the leg, ankle and foot. A lateral ankle pad is provided for the lateral side of the leg, ankle and foot. The pads are worn individually and/or together as a method of treatment for venous diseases. The pads are held in place by a constant pressure stocking, a gradient pressure stocking and/or by means of tape. The pads, placed under a pressure gradient stocking, apply even pressure to the skin around the ankle.

36 Claims, 18 Drawing Sheets

ANKLE PAD

FIELD OF THE INVENTION

This invention relates to contoured ankle pads worn generally about the ankle of a human being. An ankle pad is worn to treat ulcers which occur on the lower extremities, for example, the leg, ankle or foot. Usually, one pad is worn but two can be worn if so desired.

BACKGROUND OF THE INVENTION

Chronic venous insufficiency has plagued mankind for centuries. The result of chronic venous insufficiency at the ankle level has traditionally been that of chronic swelling, thickening of the skin, discoloration of the skin, and ultimately ulceration. Prevention of the ulceration and the chronic swelling in some people has been effected by use of heavy duty support stockings. The heavy duty support stockings have been relatively effective in many cases, however, there are a number of people, who despite the support stockings, develop a bronze discoloration and ultimately ulcerations.

Venous stasis ulcers appear as skin ulcerations on the lower extremities of a person, i.e. the leg, ankle or foot. Some of the causes of venous stasis ulcerations are known. One of the known causes of stasis ulcers is chronic venous insufficiency secondary to deep venous thrombosis or varicose veins.

It is necessary to define some terms used herein. Anterior and posterior mean nearer the front or nearer the back of the body, respectively. The median plane is an imaginary vertical plane through the body bisecting it into left and right halves. Medial means nearer the median plane and lateral means farther away from the median plane. Superficial means near the skin surface and deep means farther away from the surface. In the case of the foot, the upper surface is known as the dorsal surface and the sole is known as the plantar surface. Superior and inferior mean nearer the upper or lower end of the body respectively. The present invention discloses two ankle pads, a medial pad and a lateral pad. The medial and lateral pads and the surfaces thereof are discussed herein with respect to the left leg, ankle and foot of a human being. The exact same principles apply to the medial and lateral pads used in regard to the right leg, ankle and foot of a human being.

The two major superficial veins of the lower extremities are the great saphenous and small saphenous veins. The great saphenous vein, a superficial vein, runs generally medially and distally from the knee to the foot. The small saphenous vein, a superficial vein, runs generally posteriorly and distally from the knee down to the foot. The small saphenous vein continues into the foot and runs posteriorly and inferiorly with respect to the lateral malleolus. The great saphenous vein runs anteriorly and in proximity to the medial malleolus joining the posterior arch vein which runs posteriorly and inferiorly to the medial malleolus. The great saphenous vein communicates with the dorsal venous arch, a superficial vein of the foot.

The superficial veins are generally near the surface and communicate with deep veins which are further from the surface. Perforating veins are the veins which connect the superficial veins to the deep veins. The deep veins of the foot include the deep plantar venous arch, the medial and lateral plantar veins, and the posterior tibial veins. The deep veins of the leg include the posterior tibial veins, the peroneal veins and the anterior tibial veins. The fascia is a sheet or band of tissue which invests and connects the muscle and deep veins and holds them together.

The perforating veins are communications between the superficial veins (above the deep facia and near the skin) and the deep veins below the fascia. The deep and superficial veins possess valves which permit unidirectional flow in the direction of the heart. The perforating veins also possess valves which permit unidirectional blood flow from the superficial veins to the deep veins. The perforating veins pass through the fascia. Venous return to the heart is assisted by the pumping action of the muscles which compress the deep veins and force blood toward the heart during contraction. If the valves in the perforating veins become incompetent or if the deep veins become blocked, pressure in the superficial veins increases resulting in hyperpigmentation, eczema, edema, varicosities and/or skin ulcerations.

One cause of venous stasis is valvular insufficiency in the deep veins, perforating veins and superficial veins. Stasis means a stoppage of flow of blood. Many thousands of persons are known to be afflicted with venous stasis ulcers and the literature has addressed stasis ulcer treatment.

One article, "Stasis ulcer treatment with compression dressing" by Jess R. Young, M.D. and Barbara A. Terwood, LPN, Cleveland Clinic Journal of Medicine, pages 529–531, September 1990, discloses a hydrophilic polyurethane dressing ("ALLEVYN™") with a hydrophobic backing worn under a lightweight compression liner stocking. "ALLEVYN™" is a registered trademark of T. J. Smith and Nephew Limited. A pressure gradient stocking is worn over the lightweight pressure stocking. Other articles discussing this method of stasis ulcer treatment with compression dressing are: (1) JOBST® UlcerCARE: A Systematic Approach for Management of Venous Leg Ulcers by J. R. Young, M.D. and Barbara A. Terwood, L.P.N., Department of Vascular Medicine, Cleveland Clinic Foundation, Cleveland, Ohio; and, (2) Compression Stockings and Non-Continuous Use of Polyurethane Foam Dressings for the Treatment of Venous Ulceration, A Pilot Study, Russell H. Samson, M.D., ©1993 by Elsevier Science Publishing Co. "JOBST®" is a registered trademark of the Jobst Institute.

The stasis ulcer treatment disclosed by the three articles mentioned above involve the use of a polyurethane foam ("ALLEVYN™") or an interactive, hydrocolloidal dressing, "INTRASITE™." "INTRASITE™" is a registered trademark of T. J. Smith and Nephew Limited. The "ALLEVYN™" and "INTRASITE™" pads are flat pads of uniform thickness. They are the dressing for the ulceration.

Another article, "Treatment of venous disease—The innovators" by James A. DeWeese, M.D., Journal of Vascular Surgery, November 1994, 20:675–83, American Venous Forum, Department of Surgery, The University of Rochester, Rochester, N.Y. chronicles innovations associated with the problem of venous thrombosis. The article describes the problem as venous thrombosis of the superficial, deep and perforating veins. Venous thrombosis manifests itself as pain and swelling in early morbidity and as valvular insufficiency in late morbidity. Dr. DeWeese's article describes the innovations which have been made in the treatment of the disease, to wit, the anticoagulant heparin, filtering of the blood stream known as intraluminal partial venous interruption, balloon thrombectomy catheters, and pressure gradient stockings. Another article, "Conrad Jobst and the Development of Pressure Gradient Therapy for Venous Disease," by John J. Bergan, M.D., Surgery of the Veins, pages 529–540, ISBN D-8089-1699-8, 1985 by Grune & Stratton, discusses the innovation of a pressure gradient stocking which is worn over the foot, ankle and leg of a human being. The pressure gradient stocking and its use are well documented in the literature.

The pressure gradient stocking was developed by Conrad Jobst, a sufferer of ulcerations. Mr. Jobst found relief from his problem while standing in a swimming pool. Mr. Jobst reasoned that the water pressure in the pool, which increases with depth, cancelled out the pressure in the veins of his leg. Jobst and others have identified a need to apply a relatively large compressive force in proximity to the ankle. See, page 535 of the article entitled "Conrad Jobst and the Development of Pressure Gradient Therapy for Venous Disease." Also see, the article entitled "Treatment of venous disease—The innovators" at page 681 thereof quoting from an article by J. Horner, et al. entitled "Value of graduated compression stockings in deep venous insufficiency," Br Med J. 1980; zz: 820-1 wherein it is stated "the greater the compression gradient between the ankle and calf produced by the stocking, the lower the ambulatory pressures." The article also documents venous valvular insufficiency, the effect of gravity, the effect of muscle contraction pumping, and venous pressure about the ankle as causes of the skin ulceration.

One product on the market includes ankle pads which are sewn into an ankle stocking. This product bears the trademark JUZO®, a registered trademark of Julius Zorn, Inc. The ankle pads employed by the JUZO® device are oriented approximately about the lateral and medial aspects of the ankle. The lateral aspect of the medial ankle pad is flat as is the medial aspect of the lateral ankle pad. The pads of the JUZO® device do not contact the skin of the user because they are sewn into the ankle stocking/brace. The flatness of the pads employed in the JUZO® device limits the effectiveness of the JUZO® device. The JUZO® device does not evenly transmit pressure to areas surrounding the ankle because of the flatness of the pads with respect to the concavity of the surfaces adjacent the human ankle. Simply put, a flat pad will not fill an undulating concavity which exists adjacent the lateral malleolus and of the fibula and the medial malleolus of the tibia. Additionally, the JUZO® device is too small to fill the concavities between the bony prominences of the ankle, the Achilles tendon and the heel of a human being.

An article by Hugo Partsch, M.D., entitled "Compression Therapy of the Legs," A review, from the Department of Dermatology, Wilhelminenspital Der Stadt Wien, Vienna, Austria, Copyright 1991 by Elsevier Science Publishing Co., Inc., J. Dermatol Surg Oncol 1991; 17:799–805, at page 803, FIG. 8, illustrates the application of pads to flat parts of the lower circumference of the lower leg. The article does not illustrate application of pads to the areas adjacent the ankle. Dr. Partsch suggests that the pressure exerted by a bandage is in proportion to the radius of the leg. Therefore, flat areas of the leg, or those which have concavities do not benefit from a bandage or from a stocking because the energy or pressure from the bandage or the stocking is not transmitted where it is needed most. An article entitled "Compression Therapy" by H. A. Martino Neumann and Dig. J. Tazelaar, in Varicose Veins and Telangiectasia: Diagnosis and Treatment, St. Louis, 1993, Quality Medical, pages 103–122, describes at page 111 et seq. the physical and pathologic aspects of compression. The Neumann article at page 111 states that the: "Pressure on the leg can vary according to the surface curvature. On areas of decreased radius, for example, the malleolus, over the distal Achilles tendon, and at the sharp edge of the tibia, there is a danger of producing excessive pressure. The curvature must be flattened with padding to avoid pressure necrosis. On the other hand, pressure may be insufficient over areas in which the convex curvature is naturally low, such as the retromalleolar sulci, or convex areas, such as the dorsum of the foot. Therefor, the radius needs to be altered artificially in these areas by means of prominent pads." FIG. 7–5, page 113, of the Neumann article illustrates a pad to achieve "a good bend with the Achilles tendon." FIG. 7–6 and 7—7 of the Neumann article illustrates pads beneath bandages. These pads are large, generally tubular shaped pads. The pads shown in the Neumann article are not contoured to fill in the concavities adjacent the lateral malleolus of the fibula and the medial malleolus of the tibia. In fact, the pads shown in the Neumann article are so prominent that much of the concavities are not treated at all. The invention disclosed herein satisfies the need to treat the entire concavity with evenly applied pressure.

From an examination of the skin surface at the ankle level, it is very easy to realize that the most prominent area at the ankle is the bony prominence—the medial malleolus. There is a similar bony prominence, the lateral malleolus, on the outer aspect of the ankle, but perhaps not so marked as the medial aspect. The heel and Achilles tendon also are prominent areas, and between the medial malleolus and the heel and the Achilles tendon, is a depression in the skin. A similar depression, or concavity, exists between the lateral malleolus and the heel and the Achilles tendon. When a heavy duty support stocking is placed on the ankle, it places a great deal of pressure over the prominent areas, but there is a decreased pressure in the depressed areas, or the concavities, adjacent the medial malleolus and the lateral malleolus. Many of the chronic ulcers develop in the concavity adjacent the medial malleolus. The concavities are not compressed as well as the other areas because of the bony prominences.

The invention disclosed herein typically is placed under a stocking and fills the depression and provides additional pressure to the medial and/or lateral sides of the leg, ankle and foot of a human being. This allows for the simple application of the proper pressure gradient to the foot, ankle and leg of a patient evenly distributed to the skin, especially in the concave areas around the ankle.

The present invention is contoured to fill the concavities around the ankle as described above. The contoured shape of the lateral ankle pad and the medial ankle pad completely fills the concavities such that pressure from the compression stockings is uniformly transmitted to the concavity. According to Laplace's law cited in the article by Hugo Partsch, MD, pressure applied to the skin surface is represented by the equation: $P=(T/R)$, where (P) equals pressure, (T) equals tension and R equals the radius of curvature. Therefore, for a given tension (T) of a bandage or stocking, the pressure applied to the skin varies as the radius of curvature varies. Therefore, as the radius of curvature becomes smaller the pressure applied to the skin surface at that point is higher. As the radius of curvature becomes larger then the pressure applied to the skin surface at that point is lower.

The article entitled Compression Therapy by Neumann and Tazelaar, at pages 111–112, documents that "[o]n areas of decreased radius, for example, the malleolus, over the distal Achilles tendon, and at the sharp edge of the tibia, there is a danger of producing excessive pressure," and "[t]he curvature must be flattened with padding to avoid pressure necrosis."

The invention disclosed herein satisfies the need to equally apply the pressure to the concavities and to decrease the pressure applied to the bony prominences of the ankle and the Achilles tendon. Near the bony prominences of the ankle and the Achilles tendon the invention disclosed herein reduces the radius of curvature to relieve the excessive pressures thereat. This is accomplished, as will be seen hereinbelow, by the novel shape and contour of the medial and lateral ankle pads disclosed herein. Near the bony prominences and the Achilles tendon, the radius of curvature over which a bandage, and preferably, a stocking is applied, is increased thus lessening the pressure thereat.

In the concavities adjacent the bony prominences, the heel, and the Achilles tendon, the novel shape and contour of the lateral and medial ankle pads reduces the radius of curvature thus increasing the pressure thereat. It will be recognized by those skilled in the art that the natural radius of curvature in the concavities is relatively large and/or nonexistent thus preventing effective and even application of pressure from a bandage or stocking thereat.

The novel shape and contour of the ankle pads permits application of an even pressure to the concavities and the bony prominences, the heel and the Achilles tendon.

SUMMARY OF THE INVENTION

It is an object of the present invention to provide a simple means for the application of increased uniform external pressure to the skin of the leg, ankle and foot of a human being.

It is a further object to provide a medial ankle pad which is applied with or without dressing to the medial side of the leg, ankle and foot of a human being.

It is a further object to provide a lateral ankle pad which is applied with or without dressing to the lateral side of the leg, ankle and foot of a human being.

It is a further object to provide a medial ankle pad and/or a lateral ankle pad as described above with or without a constant pressure stocking.

It is a further object to provide a medial ankle pad and/or a lateral ankle pad as described above with or without a constant pressure stocking in combination with a pressure gradient stocking.

It is a further object of the present invention to treat venous disease of the leg, ankle and foot. The application of the aforementioned medial and lateral pads increases external pressures when the pads are worn under a pressure gradient stocking. The increase in external pressure decreases the volume of the superficial venous system, decreases the size of dilated veins, decreases soft tissue swelling, and enhances the function of the venous system of the leg, ankle and foot.

It is a further object of the present invention to provide medial and lateral ankle pads which are contoured to provide for increased compression of the ankle about the medial malleolus of the tibia and the lateral malleolus of the fibula, respectively, when a pressure gradient stocking is worn over the foot, ankle and leg.

It is a further object of the present invention to provide medial and lateral ankle pads which are hydrophobic. The pads of the present invention are preferably made of silicone elastomer. However, polyurethane foam or rubber may be used. Additionally, any other material which can be formed as described hereinbelow may be used. Different materials with different densities and/or stiffnesses may be used. This will result in proper pressure application.

It is an object of the present invention to provide medial and lateral ankle pads which conform naturally to the contour of the medial and lateral leg, ankle and foot of a human being. The preferred embodiment of the invention is lightweight and comfortable to wear.

It is an object of the present invention to provide medial and lateral ankle pads which modify the radius of curvature in the concavities between the bony prominences of the ankle, the Achilles tendon and heel of a human being.

It is an object of the present invention to provide medial and lateral pads which modify the radius of curvature at or in the proximity of the bony prominences of the ankle, the Achilles tendon, and the heel of a human being.

It is an object of the present invention to provide medial and lateral ankle pads which, in combination with a constant pressure stocking and/or a graduated pressure stocking and/or tape and/or bandaging, applies pressure evenly about and around the bony prominences of the ankle, the Achilles tendon and the heel of a human being.

Other objects and a more complete understanding of the invention will be had by referring to the brief description of the drawings, the detailed description of the preferred embodiment and the claims which follow hereinbelow.

BRIEF DESCRIPTION OF THE DRAWINGS

FIG. 1' is a sectional view of the medial pad taken along the lines 1'—1' of FIG. 1 illustrating the medial and lateral surfaces of the medial pad.

FIG. 3' is a pictorial view illustrating a piece of gauze interposed between the medial pad and the human limb.

FIG. 7' is a sectional view of the lateral pad taken along the lines 7'—7' of FIG. 7.

A more complete understanding of the drawings and the invention will be had by referring to the detailed description of the preferred embodiment which follows next hereinbelow.

DETAILED DESCRIPTION OF THE PREFERRED EMBODIMENT

Figure 1:
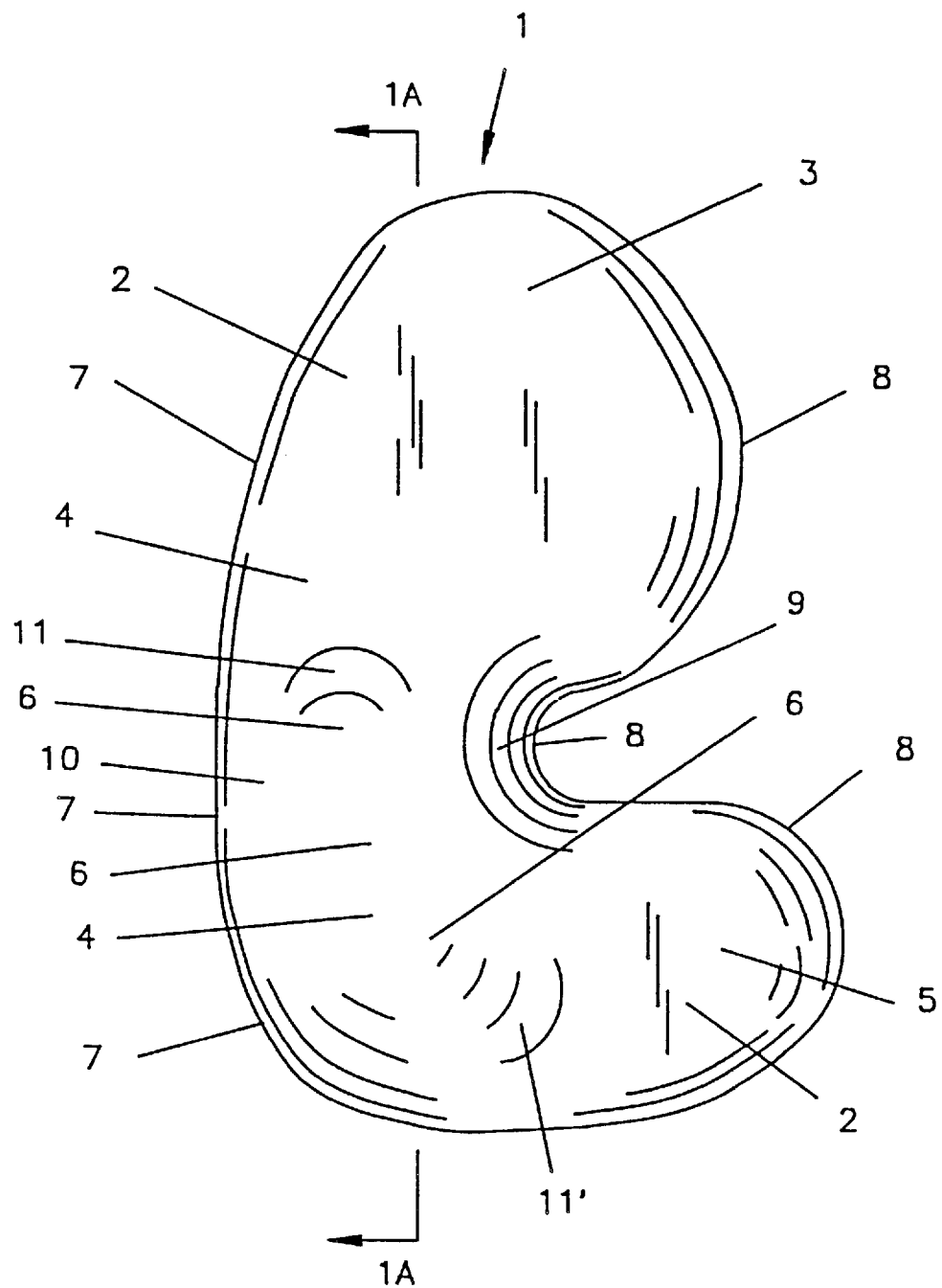
FIG. 1 is a front view of the medial pad illustrating the medial side and surfaces thereof.
Figure 1A:
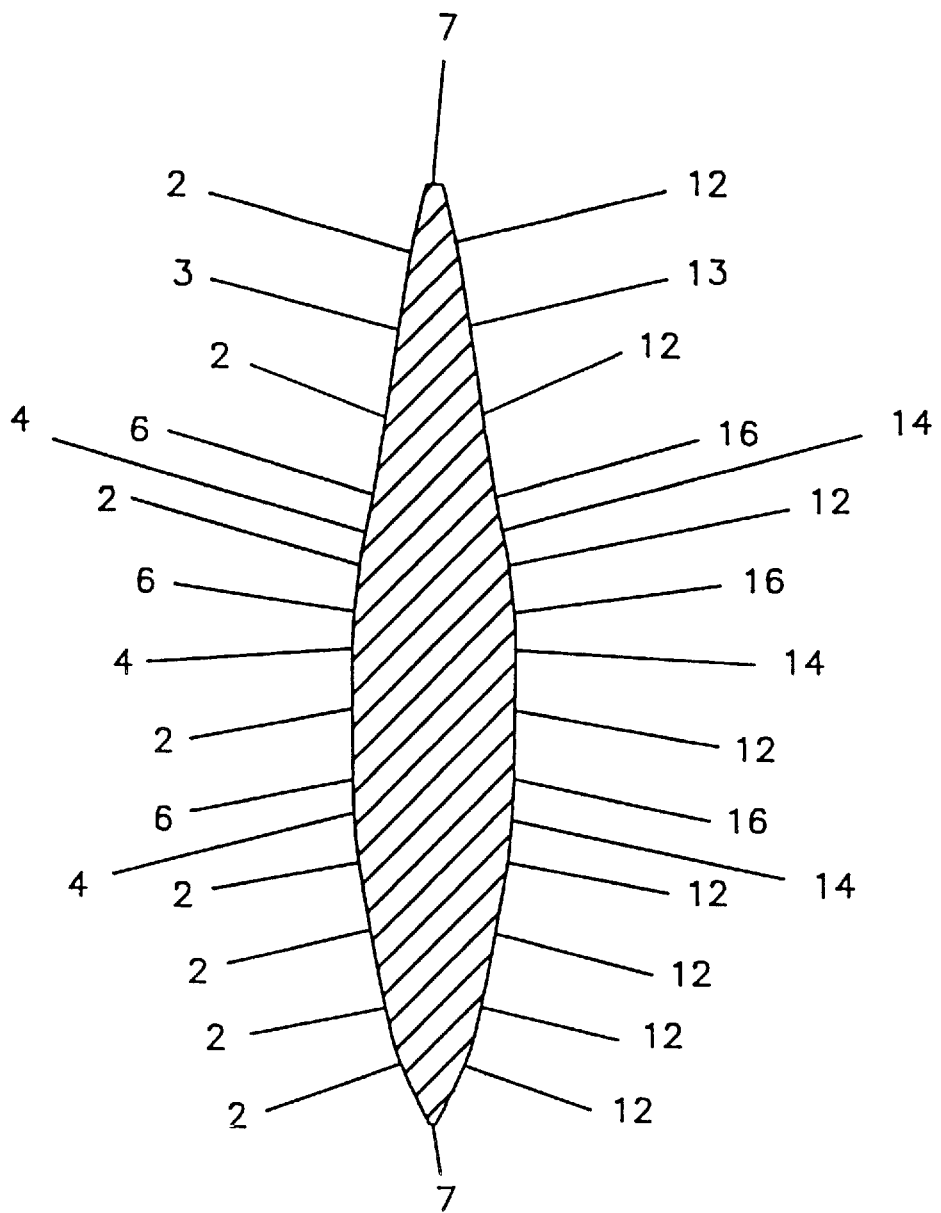

FIG. 1 is a front view of the medial pad. FIG. 1 is approximately to scale. The pad sizes, however, will vary from person to person depending on the size and anatomy of the patient. The medial pad includes a medial side 2' and a lateral side 12'. See, FIG. 6. The medial pad 1 includes medial surface 2. The medial surface 2 is comprised of a first superior portion 3, a first middle portion 4 and a first inferior portion 5. The medial surface 2 includes a crown 6 which resides generally in the first middle portion 4 of the surface 2. The medial pad 1 also includes a posterior edge 7 and an anterior edge 8.

The superior portion 3 of the medial surface 2 is a generally flat surface. The superior portion 3 of the medial surface 2 is tapered toward the posterior edge 7 and the anterior edge 8. Similarly, the first middle portion 4 which includes first crown 6 is tapered toward the posterior and anterior edges, 7 and 8, respectively.

The reference numeral 9 indicates an area with a relatively steep taper from the first crown 6 to the anterior edge 8 of the medial pad. Similarly, the reference numeral 10 indicates an area with a relatively steep taper from the first crown 6 to the posterior edge 7 of the medial pad. See, FIG. 1.

The first crown 6 is tapered in the directions of the first superior portion 3 and the first inferior portion 5 of the medial surface 2. The reference numeral 11 indicates the taper of the first crown 6 in the direction of the superior portion 3 of the medial surface 2. Similarly, reference number 11' indicates the taper of the first crown 6 in the direction of the inferior portion 5 of the medial surface 2.

FIG. 1' is a sectional view taken along lines 1'—1' of FIG. 1. FIG. 1' illustrates the contour of the medial surface 2, the first crown 6, the first middle portion 4 of the medial surface 2 and the first superior portion 3 of the medial surface 2 taken along the line 1'—1'. The posterior edge is also shown in FIG. 1'.

Figure 2:
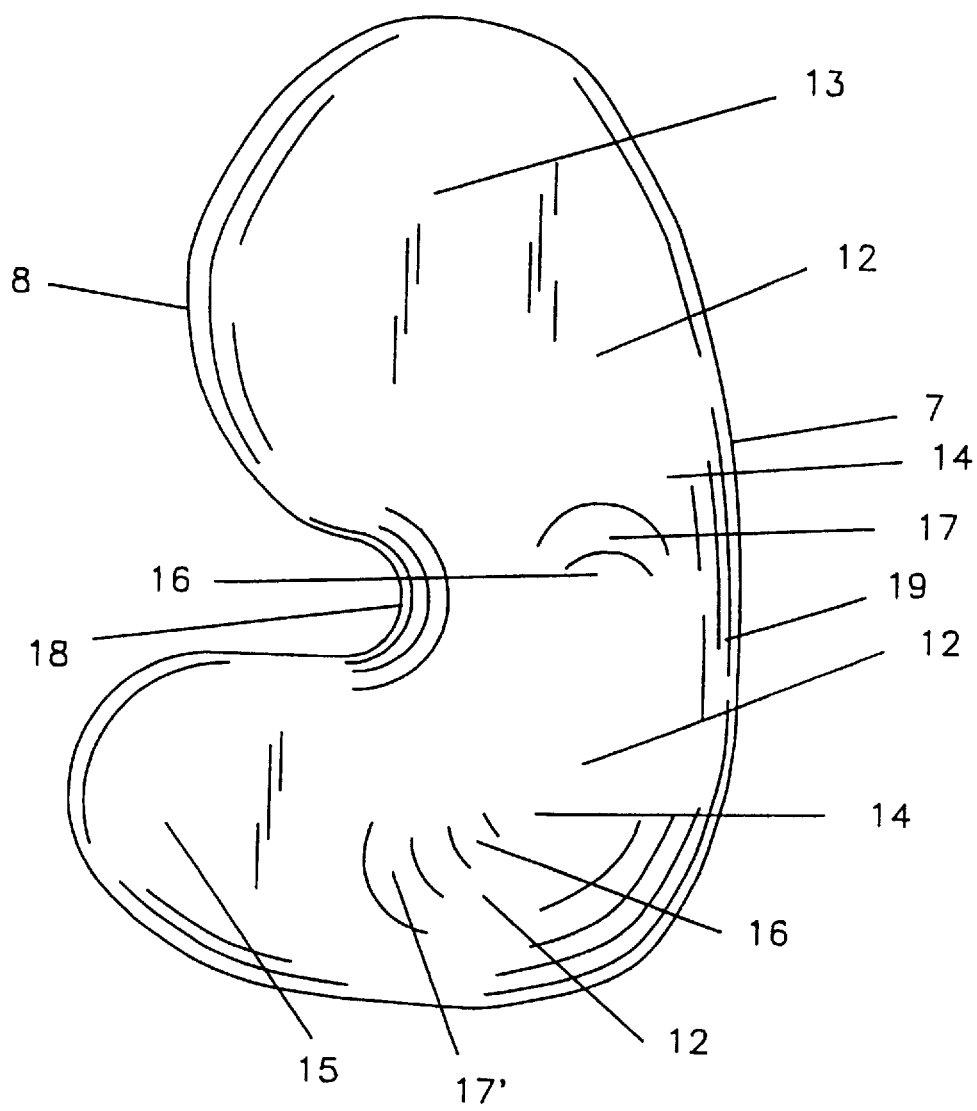
FIG. 2 is a back view of the medial pad illustrating the lateral side and surfaces thereof.

FIG. 1' also illustrates the lateral surface 12 of the medial pad 1. FIG. 2 illustrates a back view of the medial pad. FIG. 1' and FIG. 2 illustrate the lateral surface 12; the lateral surface 12 being comprised of the second superior portion 13, the second middle portion 14, the second crown 16, and the second inferior surface 15.

As shown in FIG. 2, the superior portion 13 of the lateral surface 12 is a generally flat surface. The lateral 12 and medial 2 surfaces of the medial pad are symmetrical to each other. In other words, the medial pad is symmetrical along all sections which could be taken thereof. The symmetry is shown in FIG. 1'. The lateral 12 and medial 2 surfaces of the medial pad are generally convexly shaped.

The second superior portion 13 of the lateral surface is tapered toward the posterior edge 7 and anterior edge 8. The second middle portion 14 which includes the second crown 16 is tapered the posterior and anterior edges 7 and 8, respectively. The second crown 16 is tapered in the directions of the second superior portion 13 and the second inferior portion 15 of the lateral surface 12. The reference numeral 17 indicates the taper of the second crown 16 in the direction of the second superior portion 13 of the lateral surface 12. Similarly, reference numeral 17' indicates the taper of the second crown 16 in the direction of the second inferior portion 15 of the lateral surface 12.

The reference numeral 18 indicates an area with a relatively steep taper from the second crown 16 to the anterior edge 8 of the medial pad. Similarly, the reference numeral 19 indicates a relatively steep taper from the second crown 16 to the posterior edge 7 of the medial pad. The second inferior portion 15 of the lateral surface is generally flat and is tapered toward the anterior edge 8.

Figure 3:
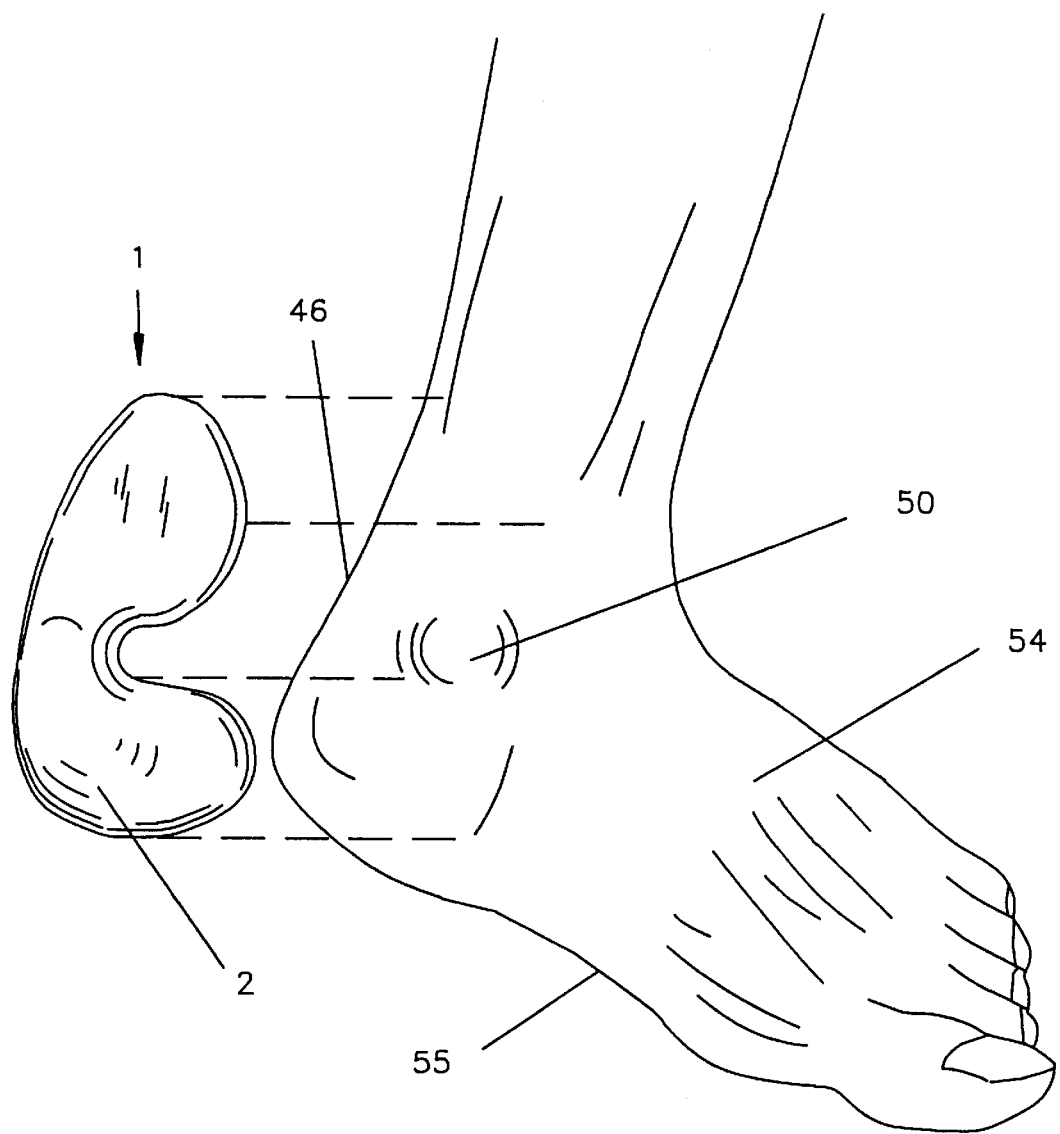
FIG. 3 is a pictorial view of the medial pad, the left leg, ankle and foot of a human being. The dashed lines indicate the approximate position of the medial pad with respect to the medial aspect of the left leg, ankle and foot of a human being. The medial pad extends considerably above the ankle to cover the lowest perforating veins.
Figure 3A:
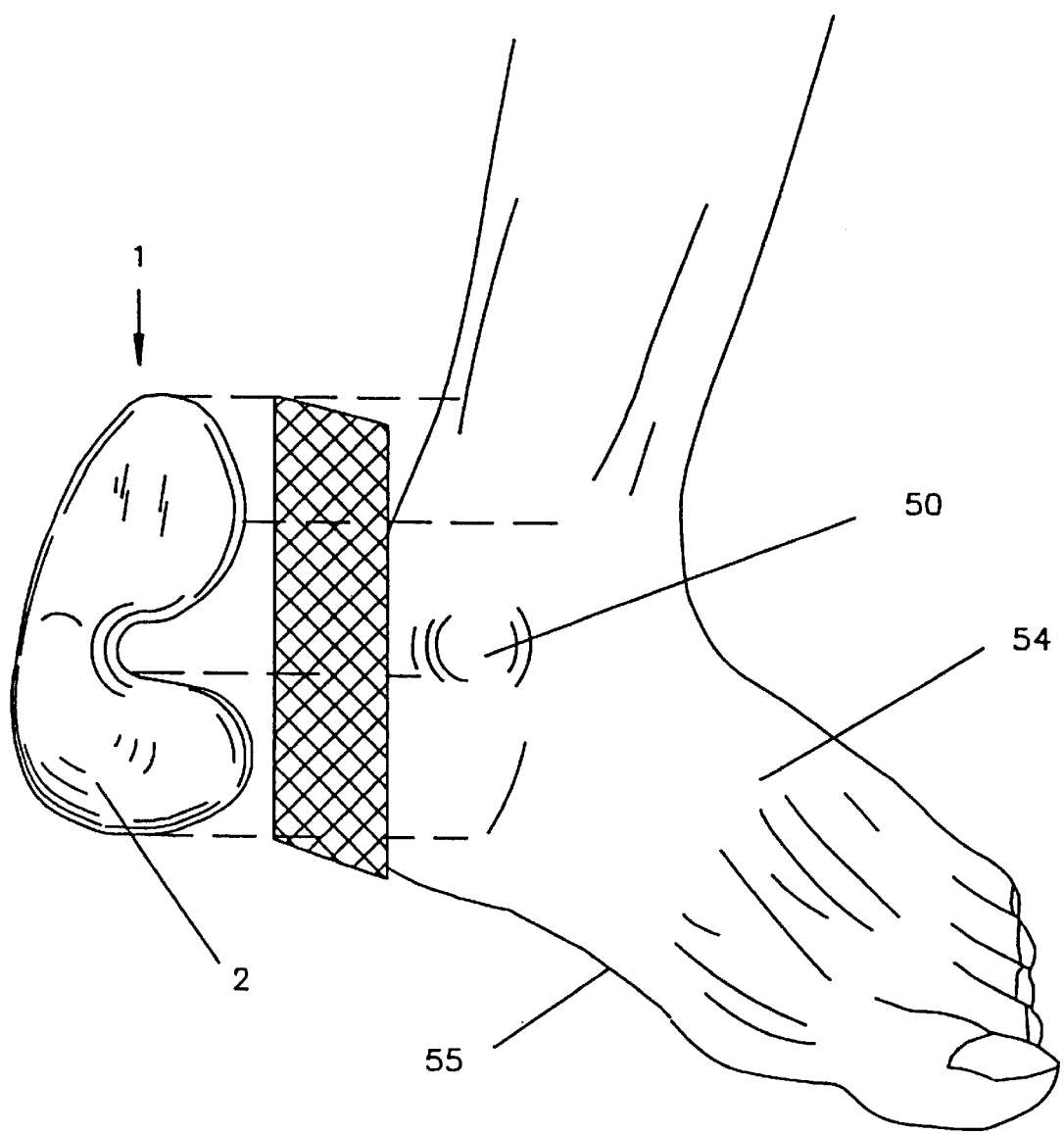

FIG. 3 is a pictorial view of the medial aspect of the left leg, ankle and foot of a human being as well as medial pad 1. The medial malleolus 50 of the tibia, the dorsal surface of the foot 54, the plantar surface of the foot 55 and the Achilles tendon 46 are also shown. The dashed lines indicate the approximate position where the pad will be located on the leg, ankle and foot.

FIG. 3' is a pictorial view similar to that shown in FIG. 3 except a piece of gauze 60, or dressing, is interposed between the silicone elastomer pad 1 and the human limb. FIG. 3' is the only drawing Figure which illustrates a dressing applied to the human limb. However, it will be understood that various dressings may be applied over ulcerations and under the medial and/or lateral pads. Wounds distal from the ankle benefit from the application of the novel pads adjacent the leg, ankle and foot as shown in FIGS. 3, 4, 5, 9, 10, 11, and 14.

Figure 4:
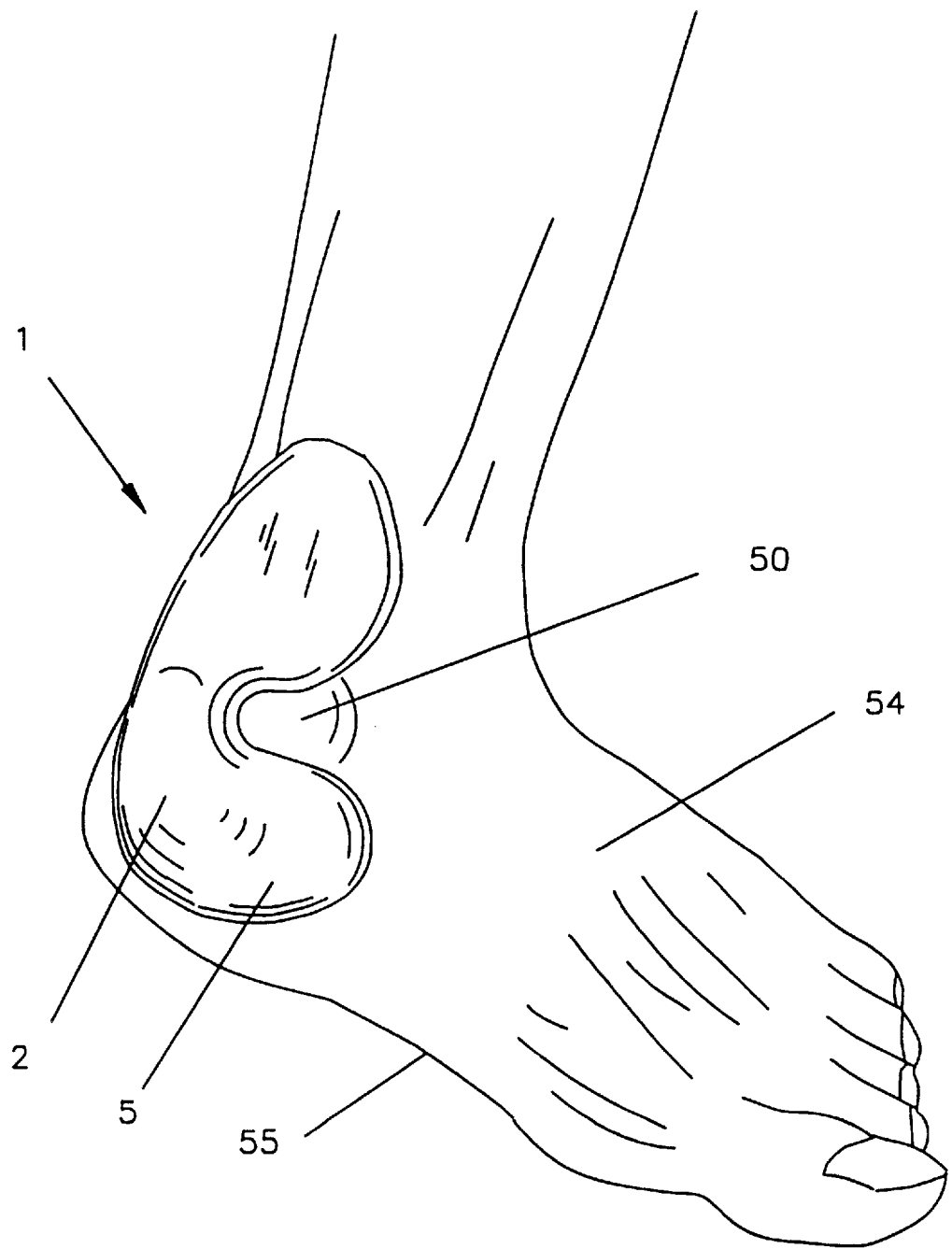
FIG. 4 illustrates application of the medial pad to the left leg, ankle and foot of a human being in a first position. Also shown in FIG. 4 are the dorsal and plantar surfaces of the foot as well as the medial malleolus of the tibia.

FIG. 4 is a pictorial view of the application of the medial pad to the left leg, ankle and foot in a first position. In the first position, the posterior of the medial pad resides in proximity to the Achilles tendon of the left foot. In the first position the first inferior portion of the medial surface of the medial pad is observed to reside slightly angularly upward with respect to the plantar, or bottom, surface of the foot.

Figure 5:
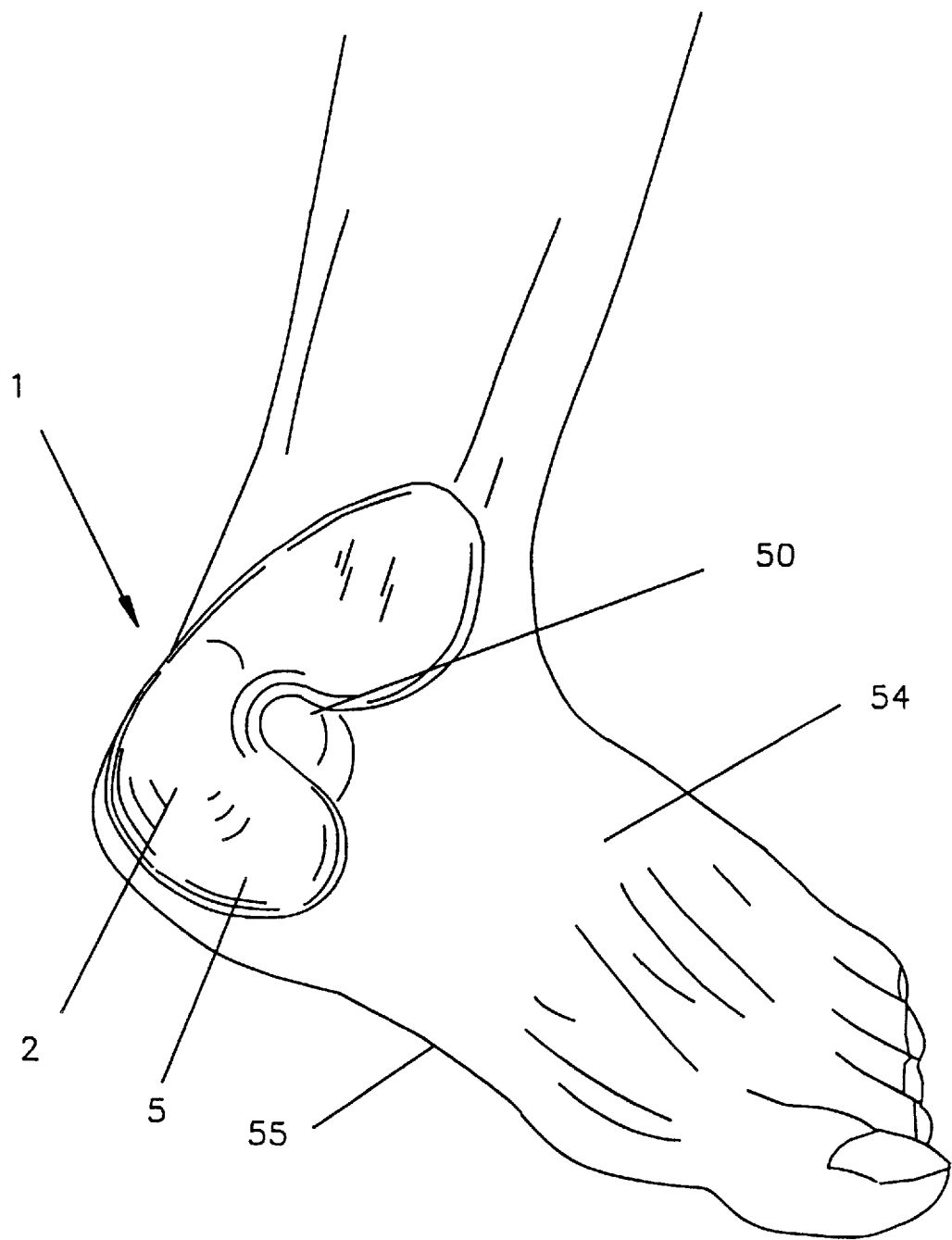
FIG. 5 illustrates the application of the medial pad to the left leg, ankle and foot of a human being in a second position. The second position illustrates the medial pad slightly rotated in a clockwise direction.

FIG. 5 is a pictorial view of the application of the medial pad to the left leg, ankle and foot in a second position. The second position of the medial pad is illustrated in FIG. 5. In the second position, the first inferior portion of the medial surface of the medial pad is substantially parallel to the plantar surface of the foot. Additionally the first superior portion of the medial surface 2 is shown substantially above the medial malleolus of the tibia. It will be understood by those skilled in the art that there are a multitude of positions in which the medial pad may be located about the medial malleolus of the tibia. Additionally, depending on the geometry and contour of the limb, differently sized and proportioned pads are specifically contemplated. The reason the pad extends substantially above the medial malleolus is to cover and compress the lowest perforating veins. Further, it will be understood that differently sized and proportioned medial and lateral pads are contemplated for a limb which has undergone trauma. It will be understood by those skilled in the art that the positioning adjustments depicted in FIGS. 4 and 5 and described hereinabove may be made to fill the concavities between the bony prominences of the ankle, the Achilles tendon and the heel where the radius of curvature is naturally large. Additionally the positioning will better effect the reduction of excessive pressures about the bony prominences, the Achilles tendon and the heel where the radius of curvature is naturally small.

Figure 6:
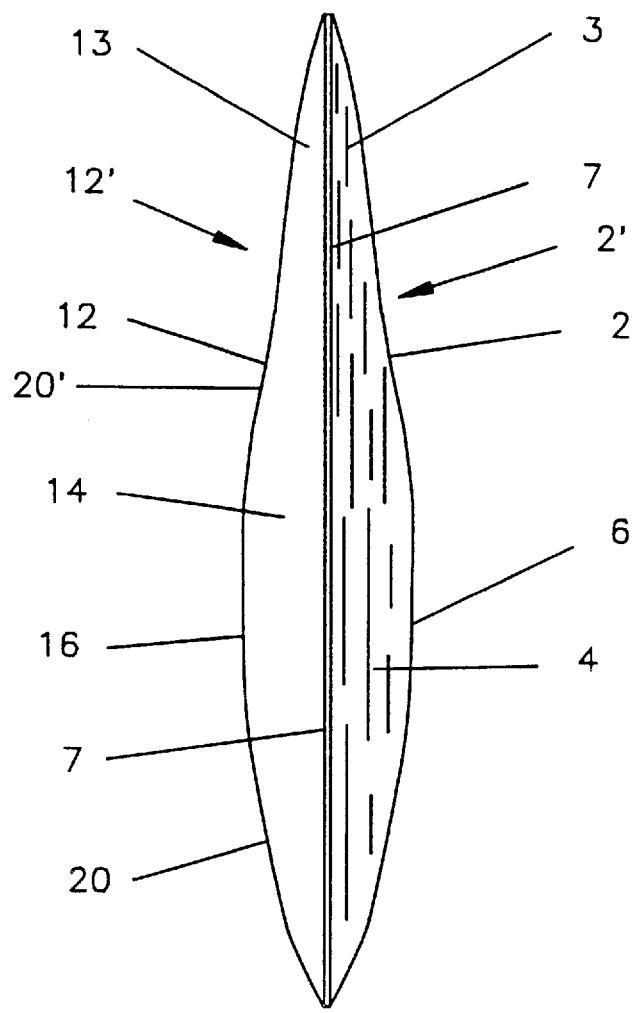
FIG. 6 is a posterior side view of the medial pad.

FIG. 6 is a posterior aspect, or side view, of the medial pad indicating the contours of the medial and lateral surfaces of the medial pad. The medial pad has the greatest breadth in the area approximately bounded by the reference numerals 20 and 20'. This shape, or contour, matches the contours of the medial side of the leg, ankle and foot. The lateral surface 12 of the lateral side 12' of the medial pad engages the medial side of the left leg, ankle and foot of a human being.

The silicone elastomer medial pad of the preferred embodiment is soft and resilient, yet when compressed, allows for an effective transfer of pressure to the area adjacent the medial malleolus of the tibia. The compression comes from one or more stockings which may be placed over the medial and/or lateral pads. Additionally, the medial and/or lateral pads may be compressed by means of tape and/or bandaging. The medial pad may be manufactured from a less resilient, stiffer, material such as rubber. This may be necessary where a higher pressure gradient is required. Sometimes, pressure gradient is referred to as pressure graduation herein. The preferred embodiment manufactured from silicone elastomer has the characteristics of being lightweight and conforms to the natural contours of the leg, ankle and foot optimizing the effect of either a constant pressure stocking or a pressure gradient stocking.

A stocking alone does not fill the natural concavities between the medial malleolus and lateral malleolus and adjacent structures of the leg, ankle and foot. The concavities are, however, filled with the medial and lateral pads evenly transmitting the pressure of the stocking applied over the pads to the concavities. The maximum pressure effect will be achieved when both the medial and lateral pads are employed under a stocking; however, only one pad may be employed. This will be discussed hereinbelow after the lateral pad is described in detail.

Figure 7:
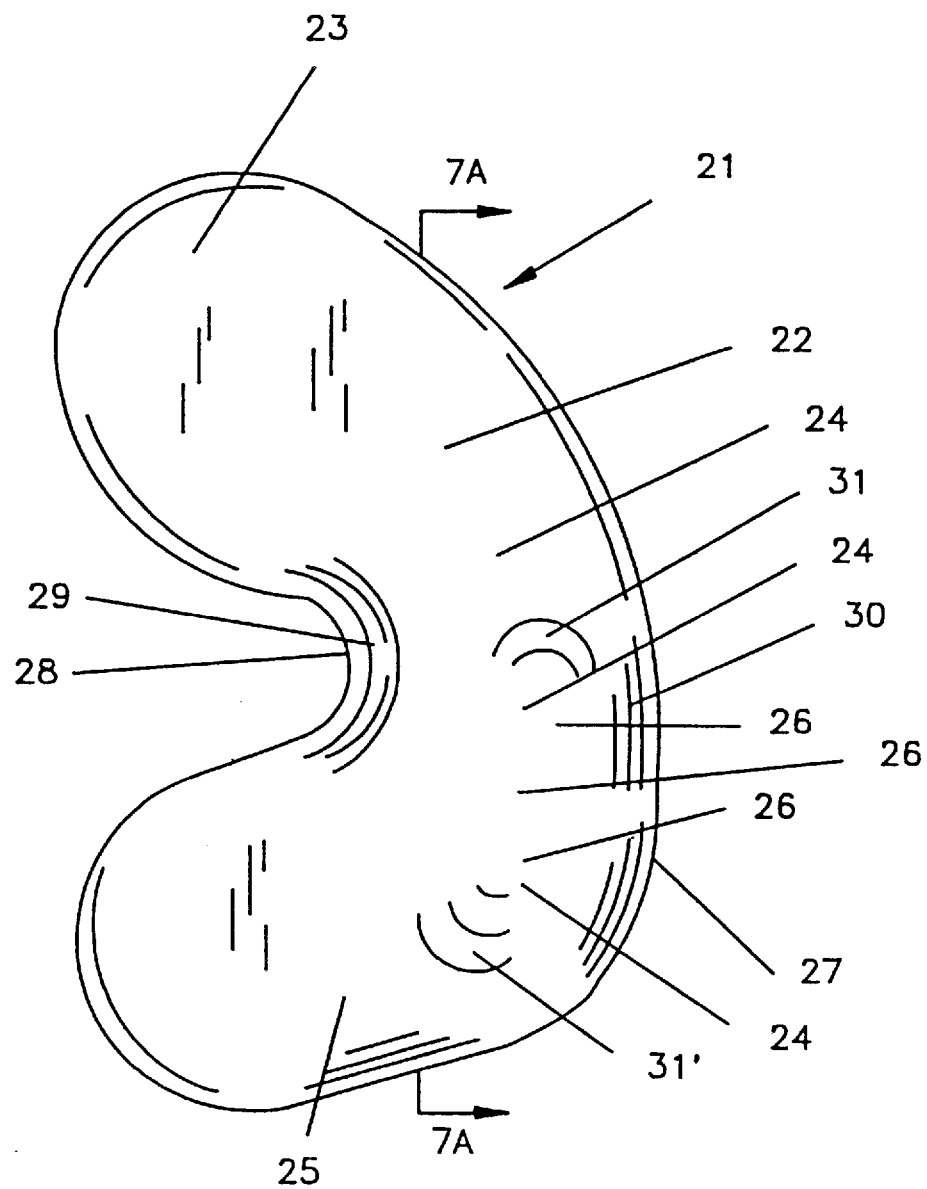
FIG. 7 is a front view of the lateral pad illustrating the lateral side and surfaces thereof.
Figure 7A:
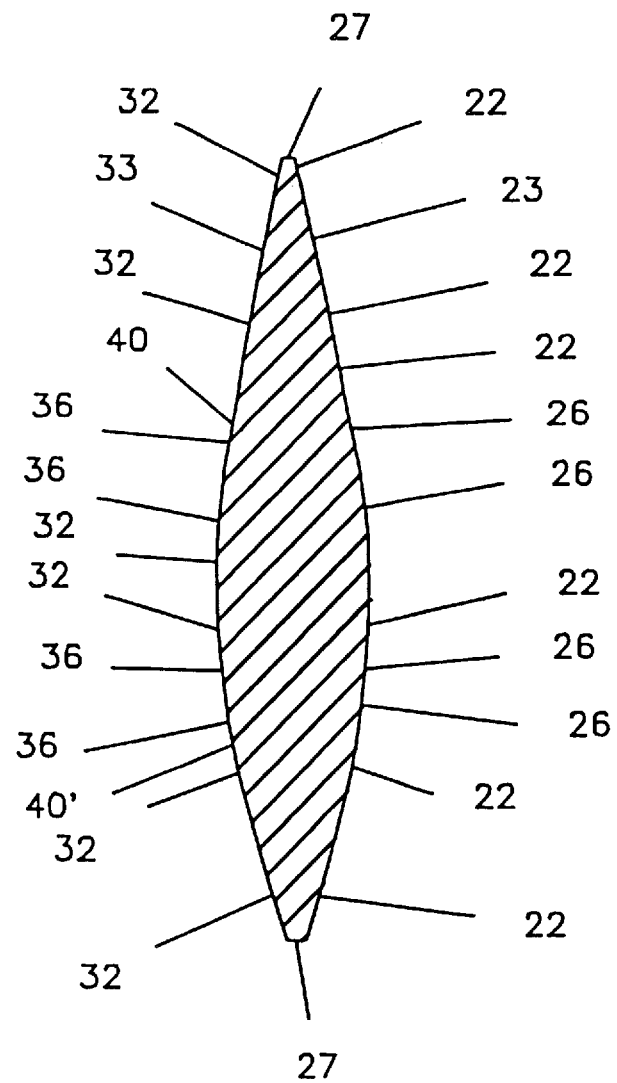

A front view of the lateral ankle pad 21 is illustrated in FIG. 7. The lateral ankle pad 21 includes a lateral side 22' and a medial side 32'. See FIG. 12. The lateral side 22' includes a lateral surface 22 and the medial side 32' includes a medial surface 32. The lateral surface 22 comprises a fourth superior portion 23, a fourth middle portion 24, and a fourth inferior portion 25 as well as a posterior edge 27 and an anterior edge 28. The fourth middle portion 24 of the lateral pad includes a fourth crown 26 thereon. See, FIGS. 7 and 7'.

The superior portion 23 of the lateral surface 22 is a generally flat surface. The superior portion 23 of the lateral surface 22 is tapered toward the posterior edge 27 and the anterior edge 28. Similarly, the fourth middle portion which includes the fourth crown 26 is tapered toward the posterior and anterior edges, 27 and 28, respectively.

The reference numeral 29 in FIG. 7 indicates an area with a relatively steep taper from the fourth crown 26 to the anterior edge 28 of the medial lateral pad 21. Similarly, the reference numeral 30 indicates an area with a relatively steep taper from the fourth crown 26 to the posterior edge 27 of the lateral pad.

The fourth crown 26 is tapered in the directions of the fourth superior portion 23 and the fourth inferior portion 25 of the lateral surface 22. The reference numeral 31 indicates the taper of the fourth crown 26 in the direction of the superior portion 23 of the lateral surface 22 of the lateral pad 21. Similarly, the reference numeral 31' indicates the taper of the fourth crown 26 in the direction of the inferior portion 25 of the lateral surface 22.

FIG. 7' is a sectional view taken along lines 7'—7' of FIG. 7. FIG. 7' illustrates the contours of the lateral surface 22, the fourth crown 26, the fourth middle portion 24 of the lateral surface 22 and the fourth superior portion 23 of the lateral surface 22 taken along the line 7'—7'.

Figure 8:
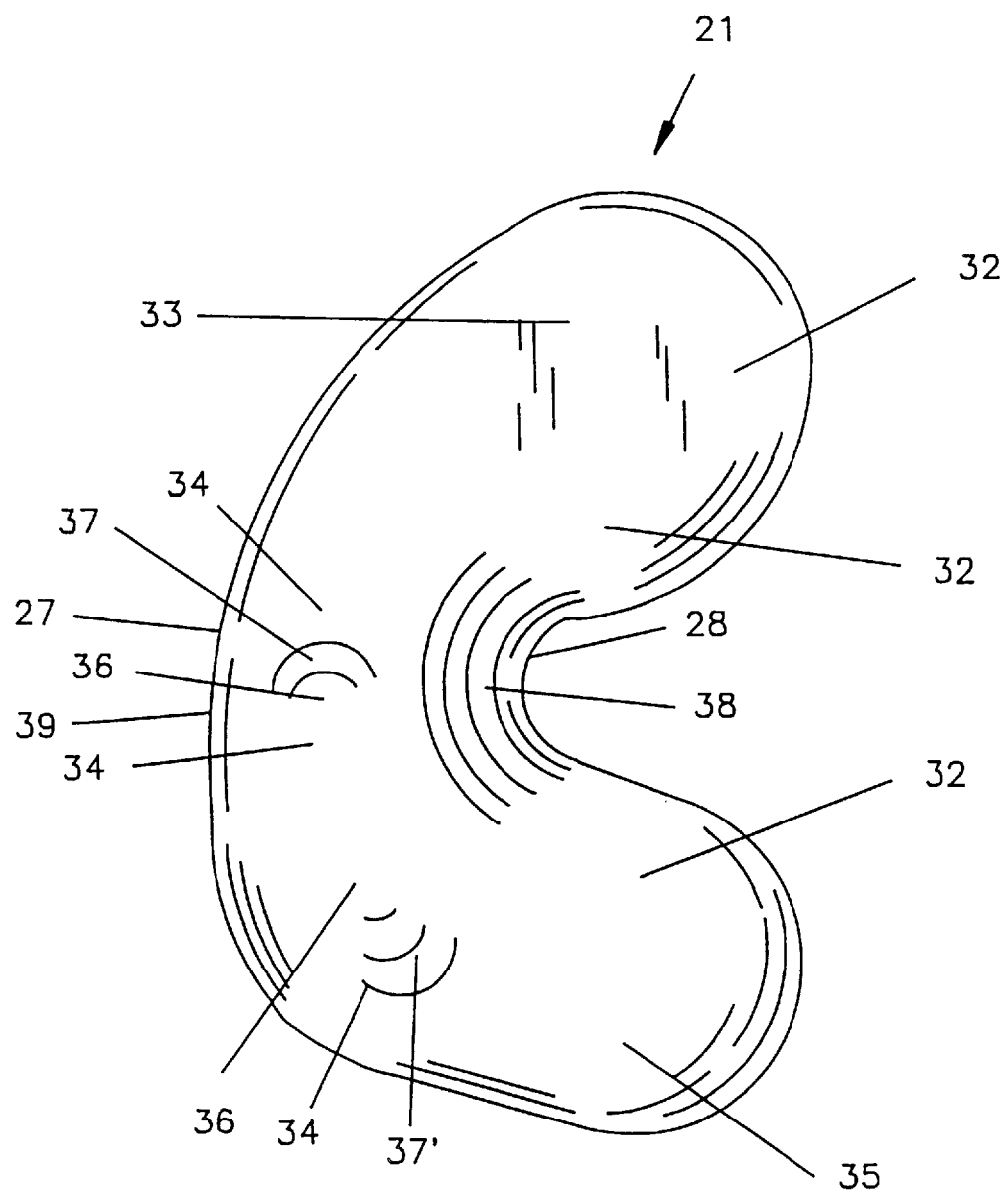
FIG. 8 is a back view of the lateral pad illustrating the medial side and surfaces thereof.

FIG. 7' also illustrates the medial surface 32 of the lateral pad. FIG. 8 illustrates a back view, or medial side view, of the lateral pad. FIG. 7' and FIG. 8 illustrate the medial surface 32; the medial surface 32 is comprised of the third superior portion 33, the third middle portion 34 of the medial surface of the lateral pad, the third crown 36, and the third inferior surface 35.

As shown in FIG. 8, the superior portion 33 of the medial surface 22 is a generally flat surface. The medial surface 32 and lateral surfaces of the lateral pad are symmetrical to each other. In other words, the lateral pad is symmetrical along all sections which could be taken thereof. The symmetry is shown in FIG. 7'. The lateral 22 and medial 32 surfaces of the lateral pad are generally convexly shaped. The medial surface 32 of the medial side 32' of the lateral pad 21 engages the lateral side of the left leg, ankle and foot of a human being.

The third superior portion 33 of the medial surface is tapered toward the posterior edge 27 and anterior edge 28. The third middle portion 34 which includes the third crown 36 is tapered toward the posterior and anterior edges 27 and 28, respectively. The third crown 36 is tapered in the directions of the third superior portion 33 and the third inferior portion 35 of the medial surface 32. The reference numeral 37 indicates the taper of the third crown 36 in the direction of the third superior portion 33 of the medial surface 32. Similarly, reference numeral 37' indicates the taper of the third crown 36 in the direction of the third inferior portion 35 of the lateral surface 32.

The reference numeral 38 indicates an area with a relatively steep taper from the third crown 36 to the anterior edge 28 of the lateral pad. Similarly, the reference numeral 39 indicates a relatively steep taper from the third crown 36 to the posterior edge 27 of the lateral pad. The third inferior portion 35 of the medial surface is generally flat and is tapered toward the anterior edge 28 of the lateral pad 21.

Figure 9:
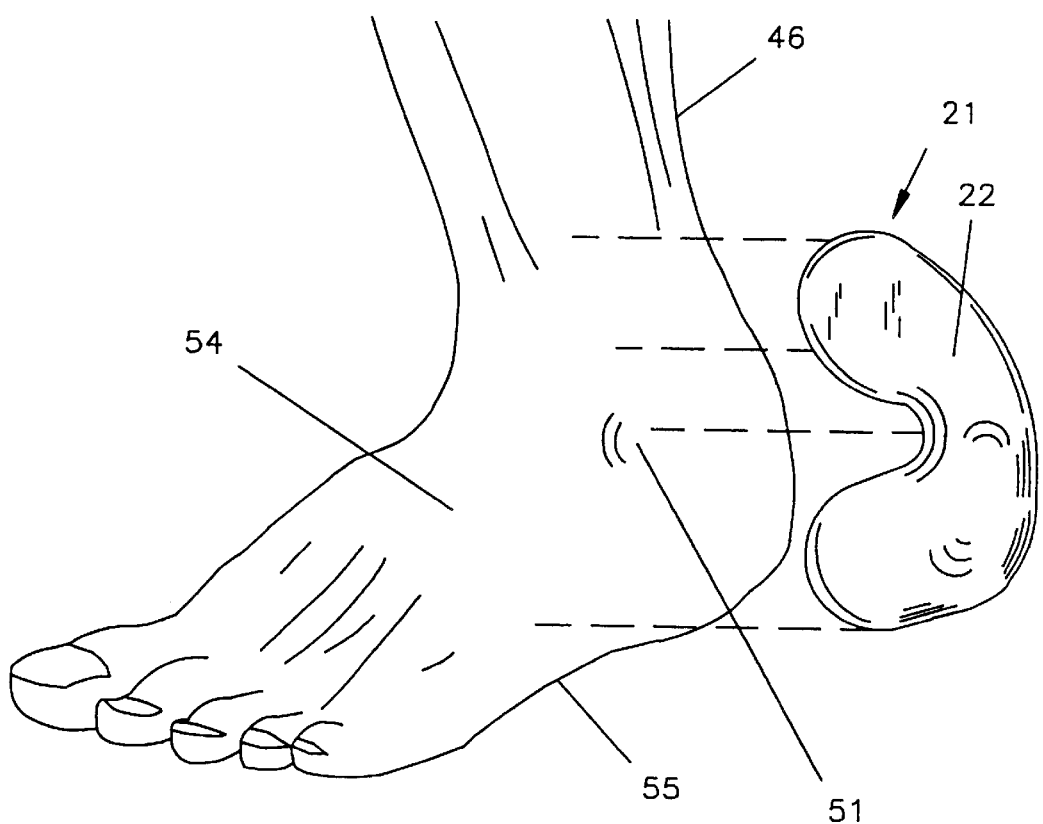
FIG. 9 is a pictorial view of the lateral pad and the left leg, ankle and foot of a human being. The dashed lines indicate the approximate position of the lateral pad with respect to the lateral aspect of the left leg, ankle and foot of a human being.

FIG. 9 is a pictorial view of the lateral aspect of the left leg, ankle and foot of a human being as well as a lateral pad 21. The lateral malleolus 51 of the fibula, the dorsal surface of the foot 54, the plantar surface of the foot 55 and the Achilles tendon 46 are also illustrated. The dashed lines indicate the approximate position where the pad will be located on the leg, ankle and foot.

Figure 10:
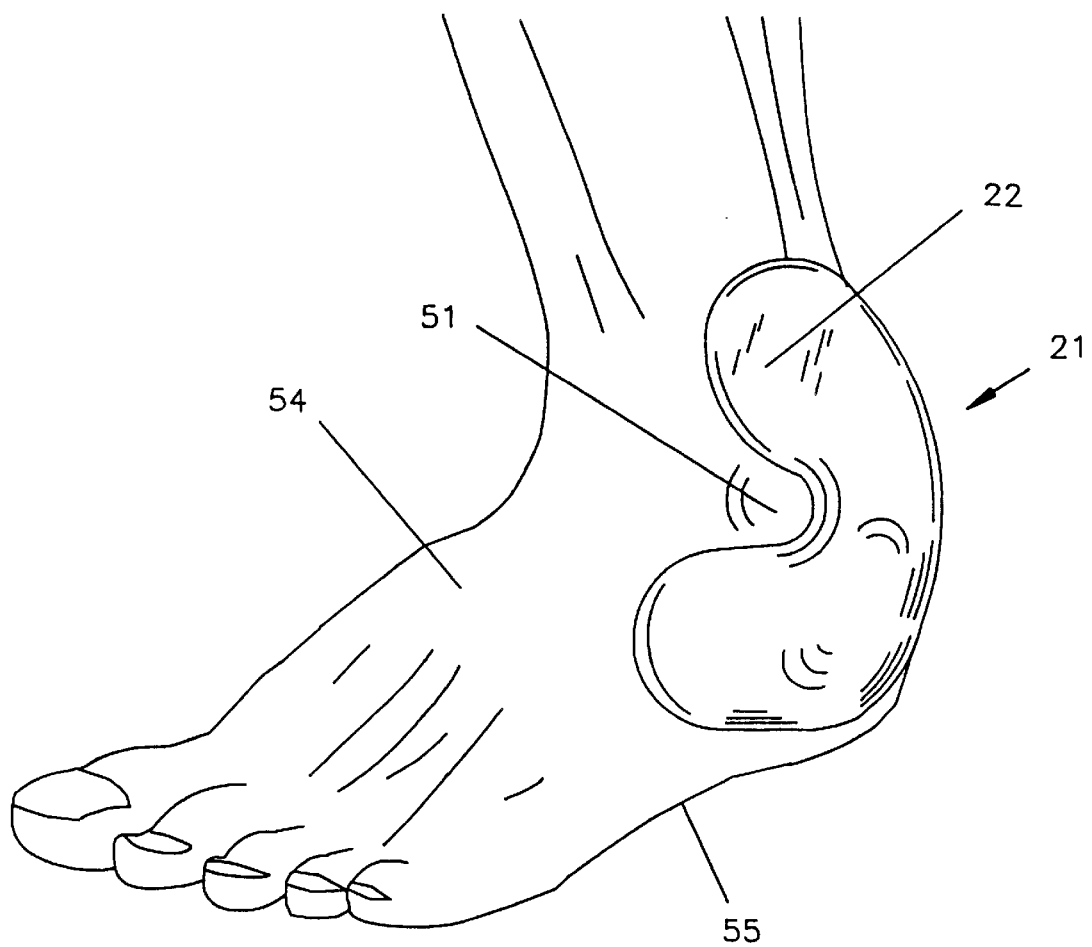
FIG. 10 illustrates application of the lateral pad to the left leg, ankle and foot of a human being in a first position. Also shown in FIG. 10 are the dorsal and plantar surfaces of the foot as well as the lateral malleolus of the fibula.

FIG. 10 is a pictorial view of the application of the lateral pad to the left leg, ankle and foot in a first position. In the first position, the posterior of the lateral pad resides in proximity to the Achilles tendon of the left foot. In the first position, the fourth inferior portion of the lateral surface of the lateral pad is observed to reside slightly angularly upward with respect to the plantar, or bottom, surface of the foot.

Figure 11:
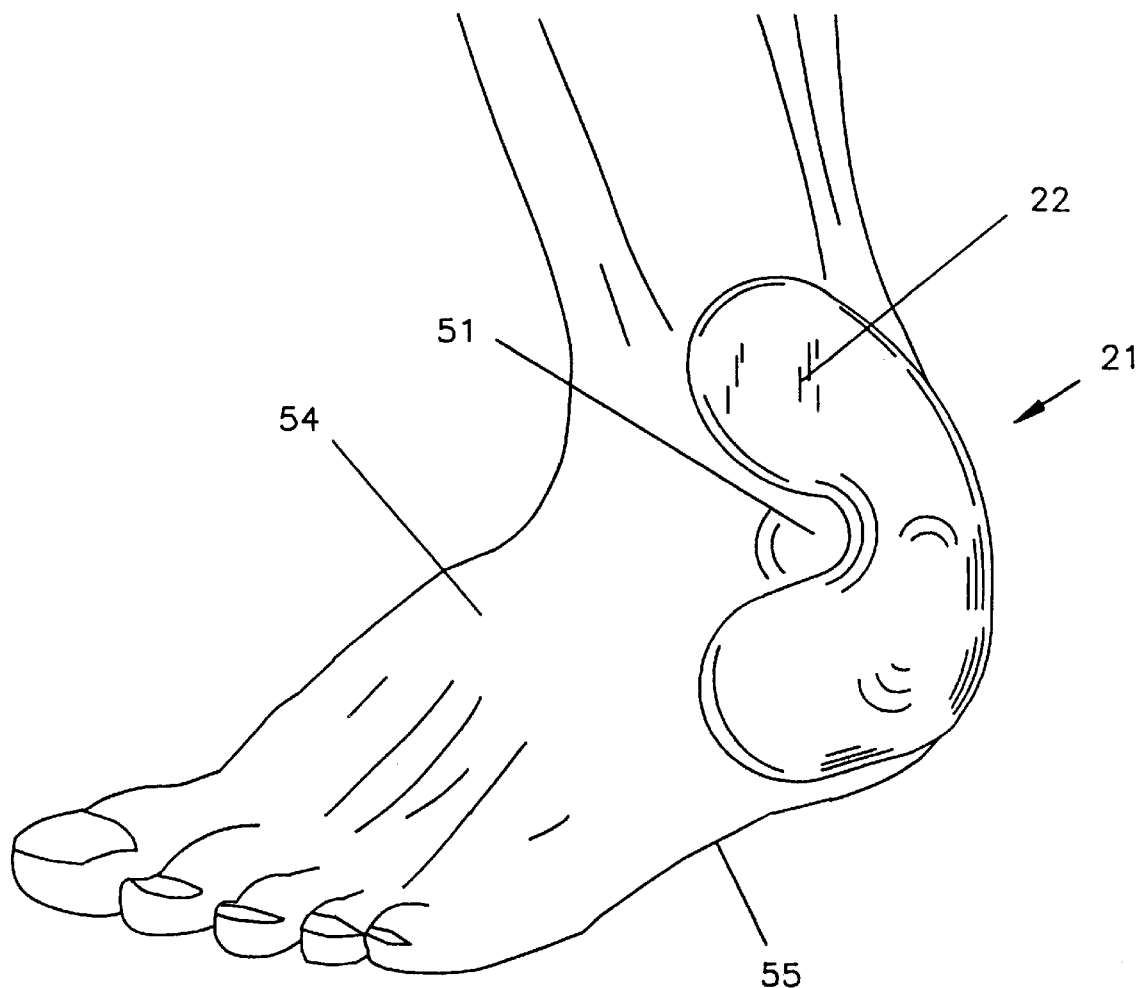
FIG. 11 illustrates application of the lateral pad to the left leg, ankle and foot of a human being in a second position. The second position illustrates the lateral pad slightly rotated in a counterclockwise direction.

FIG. 11 is a pictorial view of the application of the lateral pad to the left leg, ankle and foot in a second position. In the second position, the lateral pad is shown substantially parallel to the plantar surface of the foot. Additionally, the fourth superior portion of the lateral surface 22 is shown substantially above the lateral malleolus of the fibula. As in the case of the medial pad, it will be understood by those skilled in the art that there are a multitude of positions in which the lateral pad may be located about the lateral malleolus. Additionally differently sized and proportioned pads are specifically contemplated to accommodate for the geometric differences in the anatomy of various patients including those who have undergone trauma.

Figure 12:
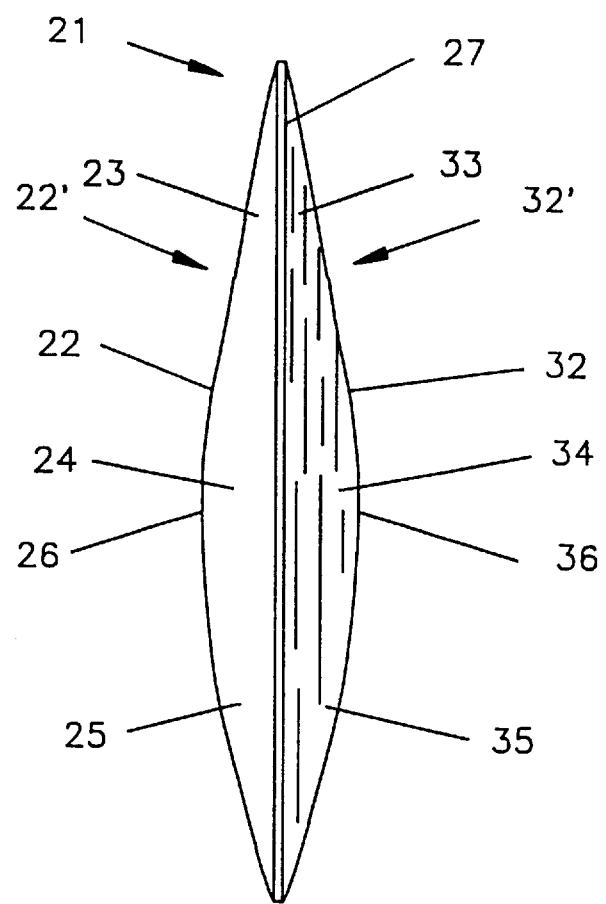
FIG. 12 is a posterior side view of the lateral pad.

FIG. 12 is a posterior aspect, or side view, of the lateral pad indicating the contours of the medial 32 and lateral 22 surfaces of the lateral pad. The lateral pad has greatest breadth in the area approximately bounded by the reference numerals 40 and 40'. See, FIG. 7'. This shape, or contour, approximates the contours of the lateral side of the leg, ankle and foot of a human being. The silicone elastomer of the preferred embodiment is soft and resilient, yet when compressed, allows for an effective transfer of pressure to the area adjacent the lateral malleolus of the fibula. As with the case of the medial pad, the compression is generated by a constant pressure and/or a pressure graduated stocking and/or tape and/or bandaging which is placed over the lateral pad.

The lateral pad is a little shorter and thinner than the medial pad. Normally, a patient will only wear one of the pads; however, two may be worn if the physician or therapist determines that two pads, in combination, will better treat the condition.

Figure 13:
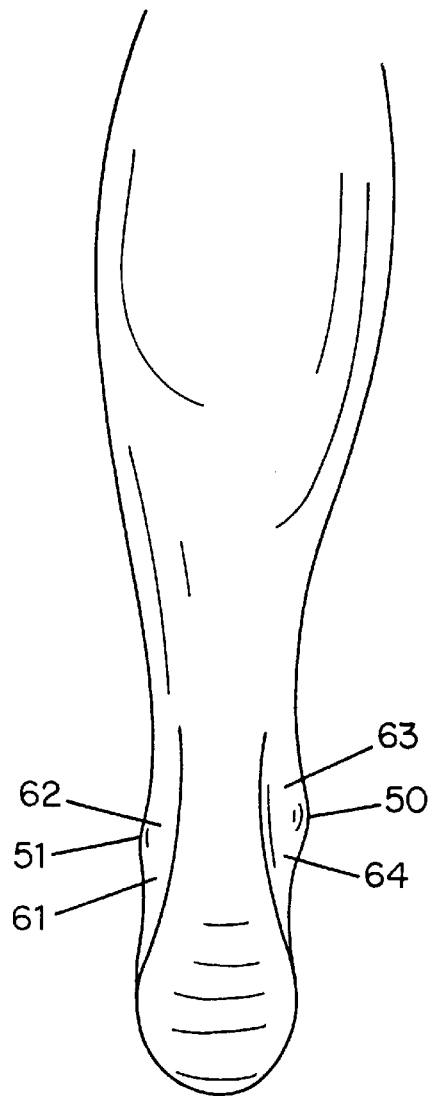
FIG. 13 illustrates the posterior aspect of the left leg, ankle and foot of a human being.

FIG. 13 is a posterior aspect of the lower left leg, ankle and foot of a human being. The contours of the skin surface adjacent the lateral 51 malleolus and medial 50 malleolus can be seen from FIG. 13. Reference numerals 61 and 62 illustrate the concavities about the lateral malleolus. Reference numerals 63 and 64 illustrate the concavities about the medial malleolus.

Figure 14:
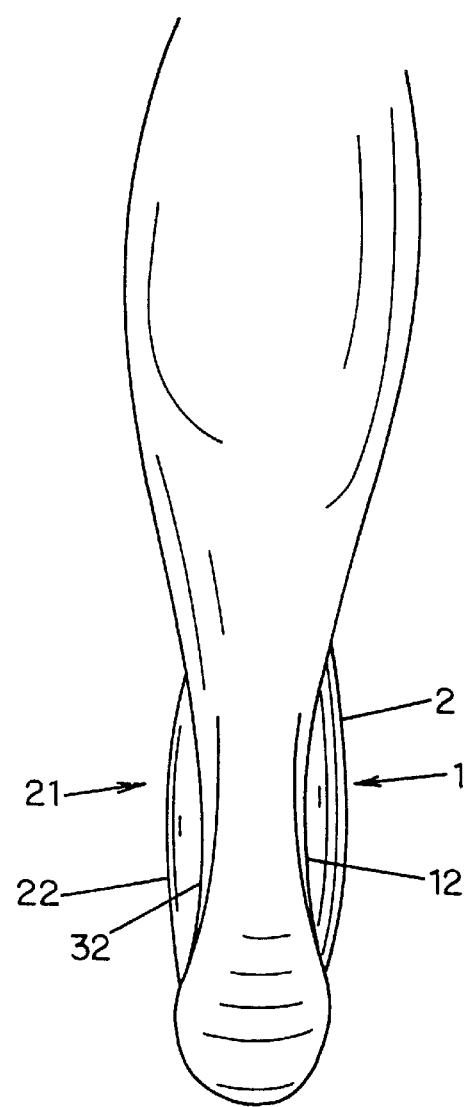
FIG. 14 illustrates the posterior aspect of the left leg, ankle and foot of a human being together with the medial and lateral pads positioned around the ankle, foot and leg. The pads can be held in position by several means known to those skilled in the art. For example, the pads can be taped in place and covered with normal street stockings. Alternatively, the pads may be held in place by a constant pressure stocking and/or a pressure gradient stocking and/or bandaging.

FIG. 14 is a posterior aspect as shown in FIG. 13 together with the medial pad 1 and the lateral pad 21 positioned with respect to the left leg, ankle and foot. It will be noted that the contours of the surfaces 12 and 32 of the medial and lateral ankle pads, respectively, match the contours of the left leg, ankle and foot. Once a stocking is placed over the medial and lateral ankle pads the posterior portions of the pads engage the Achilles tendon.

Figure 15:
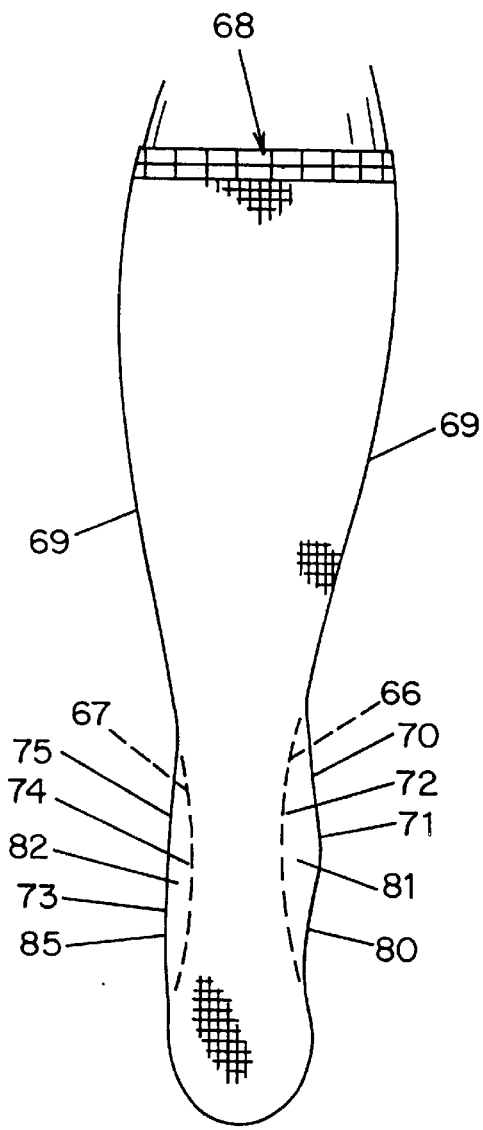
FIG. 15 illustrates the posterior aspect of the left leg, ankle and foot together with medial and lateral pads and a constant pressure stocking covering the leg, ankle and foot.

FIG. 15 is a posterior aspect of the left leg, ankle and foot similar to that shown FIGS. 13 and 14. A constant pressure stocking 68 is shown over the leg, medial ankle pad, lateral ankle pad, ankle and foot of a human being. Phantom lines represented by reference numerals 66 and 67 indicate the abutment of the medial and lateral pads against the body of the person. Reference numeral 69 indicates the fit of the constant pressure stocking over the leg. Reference numeral 70 indicates compression of the medial pad superior to the medial malleolus. Reference numerals 80 and 81 indicate compression of the medial pad inferiorly and posteriorly to the medial malleolus, respectively. On the lateral side, reference numerals 75, 82 and 85 represent compression of the lateral pad superiorly, posteriorly and inferiorly to the lateral malleolus, respectively. FIG. 15 illustrates that the lateral and medial concavities have been completely filled. This reduces the radius of curvature and effects the even application of pressure to the concavities.

Reference numerals 71 and 73 illustrate a smoothing effect adjacent the medial and lateral malleolus respectively. Reference numerals 72 and 74 illustrate a smoothing effect adjacent the medial malleolus and lateral malleolus. Smoothing effect as used herein means a modification of the radius of curvature so as to increase the radius of curvature reducing, relatively, the pressure applied to the bony prominences, the Achilles tendon and the heel in accordance with Laplace's law. This effects even application of pressure to the bony prominences, Achilles tendon, and the heel. The application of the pads has the effect of the even application of pressure about the ankle.

Figure 16:
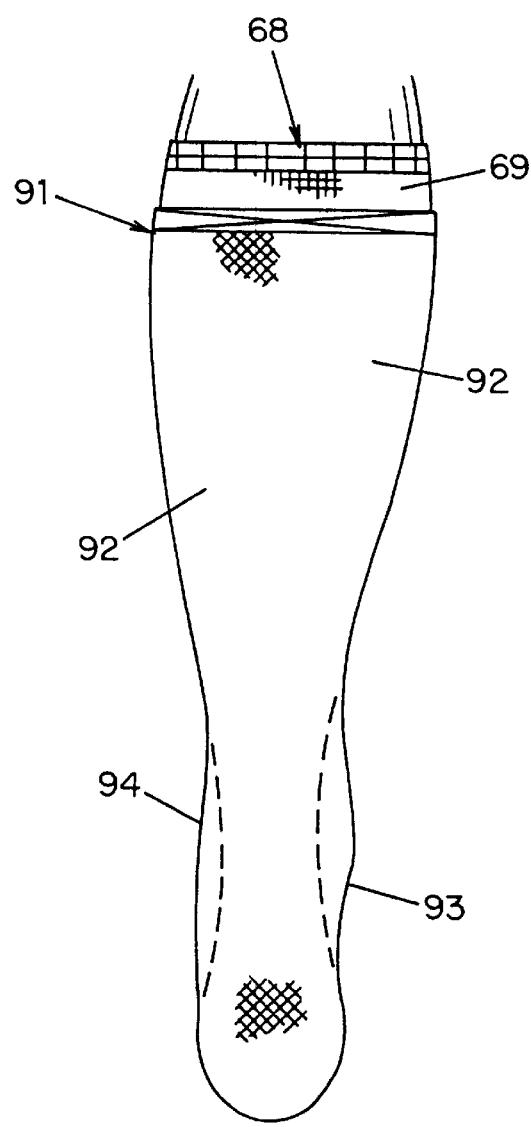
FIG. 16 illustrates the posterior aspect of the left leg, ankle and foot together with medial and lateral pads and a pressure gradient stocking over a constant pressure stocking, both of which cover the leg, ankle, foot and pads.

FIG. 16 illustrates a pressure graduated stocking 91 over the constant pressure stocking 68. Reference numeral 92 indicates the surface of the pressure gradient 91 stocking. The pressure gradient 91 stockings can be manufactured to provide different amounts of pressure at different points in the stocking. In fact, Mr. Jobst, patented a method to do so in U.S. Pat. No. 2,691,221. The medial 1 and lateral 21 pads of the present invention facilitate an even transfer of pressure to areas of the leg, ankle and foot around the lateral malleolus and medial malleolus. Reference numerals 94 and 93 indicate two exemplary locations where pressure is evenly transmitted. The constant pressure stockings and pressure gradient stockings illustrated in FIGS. 15 and 16 may extend far above the knee.

The medial and lateral pads apply pressure to the areas about the ankle where it is needed most. This has the effect of decreasing venous volume; decreasing the size of dilated veins; and, increasing the pressure gradient between the ankle and calf.

Figure 17:
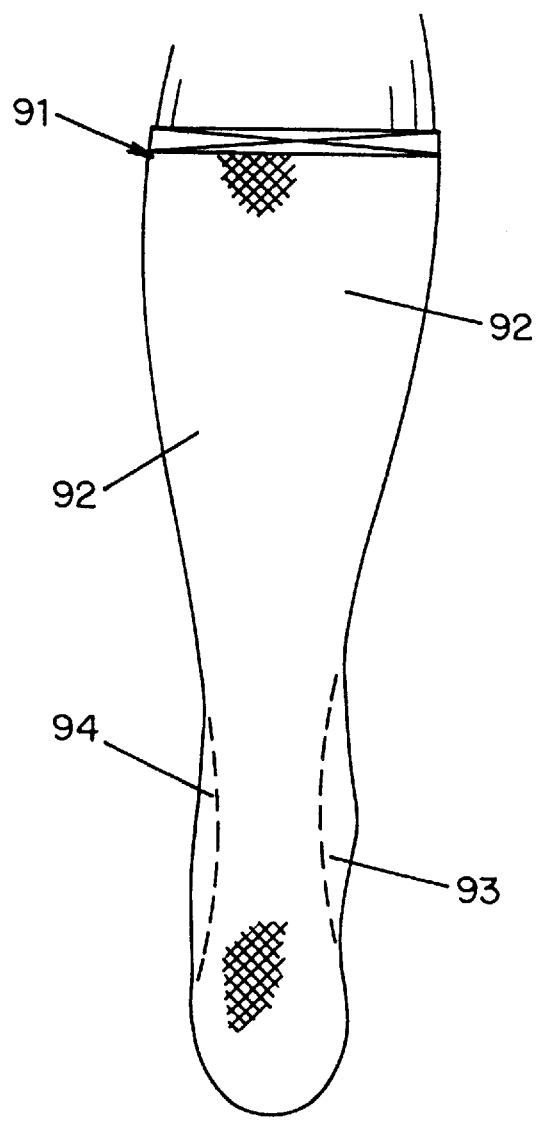
FIG. 17 illustrates the posterior aspect of the left leg, ankle and foot together with medial and lateral ankle pads and a pressure gradient stocking which covers the leg, ankle, foot and pads.

FIG. 17 is an illustration of the posterior aspect of the left leg, ankle and foot with solely a pressure graduated (gradient) stocking worn over the left leg, ankle and foot and the medial and lateral pads. The pads may be employed: with a constant compression stocking; with a pressure gradient stocking; or, with a constant pressure stocking and a pressure gradient stocking.

The medial and lateral pads of the invention fill the natural concavities in the areas surrounding and adjacent to the medial malleolus of the tibia and the lateral malleolus of the fibula.

The invention has been described in detail with particular emphasis on the preferred embodiments thereof, but it should be understood that variations and modifications within the spirit and scope of the invention may occur to those skilled in the art to which the invention pertains.

We claim:

1. A medial ankle pad comprising a medial side and a lateral side, said medial side includes a medial surface and said lateral side includes a lateral surface, said medial surface of said medial ankle pad includes a first superior portion, a first inferior portion and a first middle portion, said lateral surface of said medial ankle pad includes a second superior portion, a second inferior portion and a second middle portion, said medial surface includes a first crown thereon, and said lateral surface includes a second crown thereon.

2. A medial ankle pad as claimed in claim 1 wherein said first and second crowns reside in said first and second middle portions of said medial and lateral surfaces, respectively.

3. A medial ankle pad as claimed in claim 2 further comprising a posterior edge and an anterior edge.

4. A medial ankle pad as claimed in claim 3 wherein said first and second superior portions of said medial and lateral surfaces, respectively, are generally flat surfaces.

5. A medial ankle pad as claimed in claim 4 wherein said first and second superior portions of said medial and lateral surfaces are tapered toward said posterior and anterior edges.

6. A medial ankle pad as claimed in claim 5 wherein said first and second middle portions of said medial and lateral surfaces are tapered toward said posterior and anterior edges.

7. A medial ankle pad as claimed in claim 6 wherein said first and second inferior portions of said medial and lateral surfaces, respectively, are tapered toward said anterior edge.

8. A medial ankle pad as claimed in claim 7 wherein said pad is made of silicone elastomer.

9. A medial ankle pad as claimed in claim 7 wherein said pad is made of polyurethane foam.

10. A medial ankle pad as claimed in claim 7 wherein said pad is made of rubber.

11. A medial ankle pad as claimed in claim 7 wherein said pad is hydrophobic.

12. A medial ankle pad as claimed in claim 7 wherein said pad is generally c-shaped.

13. A medial ankle pad as claimed in claim 7 wherein said lateral surface of said medial pad engages the medial portion of the leg, ankle and foot of a human being.

14. A medial ankle pad as claimed in claim 13 wherein said superior portion of said lateral surface of said medial ankle pad is adjacent the Achilles tendon, said inferior portion of said lateral surface resides intermediate the plantar and dorsal surfaces of the foot, and said middle portion of said lateral surface being adjacent to the medial malleolus of the tibia.

15. A medial ankle pad as claimed in claim 14 in combination with a pressure gradient stocking holding and compressing said lateral surface of said medial ankle pad into engagement with and against the medial side of the leg, ankle and foot.

16. A medial ankle pad as claimed in claim 14 in combination with a constant pressure stocking holding and compressing said lateral surface of said medial ankle pad into engagement with and against the medial side of the leg, ankle and foot.

17. A medial ankle pad as claimed in claim 14 in combination with constant pressure and pressure gradient stockings holding and compressing said medial ankle pad into engagement with and against the medial side of the leg, ankle and foot.

18. A lateral ankle pad comprising a medial side and a lateral side, said medial side includes a medial surface and said lateral side includes a lateral surface, said medial surface of said lateral ankle pad includes a superior portion, a inferior portion and a middle portion and wherein said lateral surface of said lateral ankle pad includes a superior portion, an inferior portion and a middle portion, said medial surface includes a crown thereon and said lateral surface includes a crown thereon.

19. A lateral ankle pad as claimed in claim 18 wherein said crowns reside in said middle portions of said medial and lateral surfaces, respectively.

20. A lateral ankle pad as claimed in claim 19 further comprising a posterior edge and an anterior edge.

21. A lateral ankle pad as claimed in claim 20 wherein said superior portions of said medial and lateral surfaces, respectively, are generally flat surfaces.

22. A lateral ankle pad as claimed in claim 21 wherein said superior portions of said medial and lateral surfaces are tapered toward said posterior and anterior edges.

23. A lateral ankle pad as claimed in claim 22 wherein said middle portions of said medial and lateral surfaces are tapered toward said posterior and anterior edges.

24. A lateral ankle pad as claimed in claim 23 wherein said inferior portions of said medial and lateral surfaces are tapered toward said anterior edge.

25. A lateral ankle pad as claimed in claim 24 wherein said pad is made of silicone elastomer.

26. A lateral ankle pad as claimed in claim 24 wherein said pad is made of polyurethane foam.

27. A lateral ankle pad as claimed in claim 24 wherein said pad is made of rubber.

28. A lateral ankle pad as claimed in claim 24 wherein said pad is hydrophobic.

29. A lateral ankle pad as claimed in claim 24 wherein said pad is generally c-shaped.

30. A lateral ankle pad as claimed in claim 24 wherein said medial surface of said lateral pad engages the lateral portion of the leg, ankle, and foot of a human being.

31. A lateral ankle pad as claimed in claim 30 wherein said superior portion of said medial surface is adjacent the Achilles tendon, said inferior portion of said medial surface resides intermediate the plantar and dorsal surfaces of the foot, and said middle portion of said medial surface being adjacent to the lateral malleolus of the fibula.

32. A lateral ankle pad as claimed in claim 31 in combination with a pressure gradient stocking holding and compressing said lateral ankle pad into engagement with and against the lateral side of the leg, ankle and foot.

33. A lateral ankle pad as claimed in claim 31 in combination with a constant pressure stocking holding and compressing said lateral ankle pad into engagement with and against the lateral side of the leg, ankle and foot.

34. A lateral ankle pad as claimed in claim 31 in combination with constant pressure and pressure gradient stockings holding and compressing said lateral ankle pad into engagement with and against the lateral side of the leg, ankle and foot.

35. A medial ankle pad comprising a medial side and a lateral side contoured to increase the radius of curvature at and around the bony prominences, Achilles tendon and heel of a human being and to decrease the radius of curvature of the concavities between the bony prominences, Achilles tendon and heel of a human being such that pressure is applied evenly when said medial ankle pad is worn under a stocking.

36. A lateral ankle pad comprising a medial side and a lateral side contoured to increase the radius of curvature at and around the bony prominences, Achilles tendon and heel of a human being and to decrease the radius of curvature of the concavities between the bony prominences, Achilles tendon and heel of a human being such that pressure is applied evenly when said lateral ankle pad is worn under a stocking.

* * * * *

UNITED STATES PATENT AND TRADEMARK OFFICE
CERTIFICATE OF CORRECTION

PATENT NO. : 5,823,195
DATED : October 20, 1998
INVENTOR(S) : C. David Shook and David J. Hoy It is certified that error appears in the above-identified patent and that said Letters Patent is hereby corrected as shown below:

Column 6, line 22, after "FIG." delete " 1' " and insert --1A--.
Column 6, line 23, after "lines" delete " 1'—1' " and insert --1A-1A--.
Column 6, line 33, after "FIG." delete " 3' " and insert --3A--.
Column 6, line 47, after "FIG." delete "7' " and insert --7A--.
Column 6, line 48, after "lines" delete " 7'—7' " and insert --7A-7A--.
Column 7, line 60, after "FIG." (first occurrence) delete " 1' " and insert --1A--.
Column 7, line 60, after "lines" delete " 1'—1' " and insert --1A-1A--.
Column 7, line 61, after "FIG." delete " 1' " and insert --1A--.
Column 7, line 64, after "line" delete " 1'—1' " and insert --1A-1A--.
Column 7, line 65, after "FIG." delete " 1' " and insert --1A--.
Column 7, line 66, after "FIG." delete " 1' " and insert --1A--.
Column 8, line 1, after "FIG." delete " 1' " and insert --1A--.
Column 8, line 10, after "FIG." delete " 1' " and insert --1A--.
Column 8, line 39, after "FIG." (first occurrence) delete " 3' " and insert --3A--.
Column 8, line 42, after "FIG." delete "3' " and insert --3A--.
Column 9, line 59, "7' " and insert --7A--.
Column 10, line 13, after "FIG." (first occurrence) delete "7' " and insert --7A--.
Column 10, line 13, after "lines" delete " 7'—7' " and insert --7A-7A--.
Column 10, line 14, after "FIG." delete " 7' " and insert --7A--.
Column 10, line 17, after "line" delete " 7'—7' " and insert --7A-7A--.
Column 10, line 18, after "FIG." delete " 7' " and insert --7A--.
Column 10, line 20, after "FIG." delete " 7' " and insert --7A--.

UNITED STATES PATENT AND TRADEMARK OFFICE
CERTIFICATE OF CORRECTION

PATENT NO. : 5,823,195
DATED : October 20, 1998
INVENTOR(S) : C. David Shook and David J. Hoy It is certified that error appears in the above-identified patent and that said Letters Patent is hereby corrected as shown below:

Column 10, line 29, after "FIG." delete " 7' " and insert --7A--.
Column 11, line 18, after "FIG." delete " 7' " and insert --7A--.

Signed and Sealed this

Ninth Day of May, 2000

Attest:

Q. TODD DICKINSON

Attesting Officer

Director of Patents and Trademarks